United States Patent [19]

Battistini et al.

[11] Patent Number: 5,922,750
[45] Date of Patent: Jul. 13, 1999

[54] TERPENOIDIC DERIVATIVES USEFUL AS ANTITUMOR AGENTS

[75] Inventors: Carlo Battistini, Novate Milanese; Marina Ciomei, Torre d'Isola; Francesco Pietra, Lucca; Michele D'Ambrosio, Povo; Antonio Guerriero, Trento, all of Italy

[73] Assignee: Pharmacia & Upjohn S.p.A., Milan, Italy

[21] Appl. No.: 09/131,290

[22] Filed: Aug. 7, 1998

Related U.S. Application Data

[62] Division of application No. 08/765,436, Jan. 15, 1997., Pat. No. 5,869,514, filed as application No. PCT/EP96/01688, Apr. 23, 1996.

[30] Foreign Application Priority Data

May 16, 1995 [GB] United Kingdom .................... 9509888

[51] Int. Cl.[6] ........................ A61K 31/415; C07D 233/64
[52] U.S. Cl. ......................................... 514/397; 548/311.4
[58] Field of Search ........................ 514/397; 548/311.14

[56] References Cited

U.S. PATENT DOCUMENTS

| | | | |
|---|---|---|---|
| 4,861,776 | 8/1989 | Nelson et al. | 514/233.5 |
| 5,204,364 | 4/1993 | Carganico et al. | 514/399 |

OTHER PUBLICATIONS

D'Ambrosio et al, Helv. Chim. Acta (1987), 70(8), 2019,27.
D'Ambrosio et al, Helv. Chim. Acta (1987), 70(8), 2019, 27.
Honda et al, Prostaglandins, vol. 36, No. 5, Nov. 1988, pp. 621–630.

*Primary Examiner*—Laura L. Stockton
*Attorney, Agent, or Firm*—Oblon, Spivak, McClelland, Maier & Neustadt, P.C.

[57] ABSTRACT

The present invention relates to terpenoidic derivatives, known in the art as Sarcodictyins, for use as therapeutic agents, and to pharmaceutical compositions containing them.

In particular, Sarcodictyins can be useful as therapeutic antineoplastic agents in the treatment of cancers in human or animal beings.

7 Claims, No Drawings

TERPENOIDIC DERIVATIVES USEFUL AS ANTITUMOR AGENTS

This application is a Division of application Ser. No. 08/765,436, filed on Jan. 15, 1997 now U.S. Pat. No. 5,869,514, which was filed as International Application No. PCT/EP96/01688 on Apr. 23, 1996.

The present invention relates to terpenoidic derivatives, known in the art as Sarcodictyins (Helvetica Chimica Acta Vol. 70, 1987, 2019–2027 and Helvetica Chimica Acta, Vol. 71, 1988, 964–976), which can be useful as therapeutic agents.

A possible therapeutic application of the Sarcodictyins mentioned in the present application was not reported earlier.

In particular, according to the present invention, Sarcodictyins, in view of their cytotoxic activity, can be of use as therapeutic antineoplastic agents in the treatment of cancers in human or animal beings.

Accordingly, the present invention refers to a compound selected from the group consisting of:

(−)-(4R,4aR,7R,10S,11S,12aR,1Z,5E,8Z)-7,10-Epoxy-3,4,4a,7,10,11,12,12a-octahydro-7-hydroxy-6-(methoxycarbonyl)-1,10-dimethyl-4-(1-methylethyl)benzocyclodecen-11-yl (E)-3-(1-Methyl-1H-imidazol-4yl) acrylate (Sarcodictyin A);

(−)-(4R,4aR,7R,10S,11S,12aR,1Z,5E,8Z)-7,10-Epoxy-6-(ethoxycarbonyl)-3,4,4a,7,10,11,12,12a-octahydro-7-hydroxy-1,10-dimethyl-4-(1-methylethyl)benzocyclodecen-11-yl (E)-3-(1-Methyl-1H,imidazol-4-yl)acrylate (Sarcodictyin B);

(−)-(3R,4S,4aS,7S,10R,11R,12aS,1Z,5E,8Z)-7,10-Epoxy-3,4,4a,7,10,11,12,12a,octahydro-3,7-dihydroxy-6-(methoxycarbonyl)-1,10-dimethyl-4-(1-methylethyl)benzocyclodecen-11-yl (E)-3-(1-Methyl-1H-imidazol-4-yl)acrylate (Sarcodictyin C);

(−)-(3R,4S,4aS,7S,10R,11R,12aS,1Z,5E,8Z)-3-Acetoxy-7,10-epoxy-3,4,4a,7,10,11,12,12a-octahydro-7-hydroxy-6-(methoxycarbonyl)-1,10-dimethyl-4-(1-methylethyl)benzocyclodecen-11-yl(E)-3-(1-Methyl-1H-imidazol-4-yl)acrylate (Sarcodictyin D);

(+)-(3R,4S,4aS,7S,10R,11R,12aS,1Z,5E,8Z)-7,10-Epoxy-3,4,4a,7,10,11,12,12a-octahydro-3,7-dihydroxy-6-(methoxycarbonyl)-1,10-dimethyl-4-(1-methylethyl)benzocyclodecen-11-yl(Z)-3-(1-Methyl-1H-imidazol-4-yl)acrylate (Sarcodictyin E); and (+)-(1R,4R,4aR,7R,10S,11S,12aR,2Z,5E,8Z)-7,10-Epoxy-1,4,4a,7,10,11,12,12a-octahydro-1,7-dihydroxy-6-(methoxycarbonyl)-1,10-dimethyl-4-(1-methylethyl)benzocyclodecen-11-yl (E)-3-(1-Methyl-1H-imidazol-4-yl)acrylate (Sarcodictyin F);

for use as a therapeutic agent.

The structural formulae of the above listed compounds is reported in Table 1 below, with reference to the following formulae:

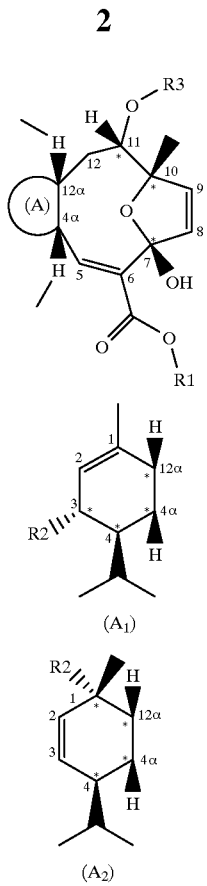

In the above formulae, the symbol * represent a chiral center.

TABLE 1

| COMPOUND | (A) | $R_1$ | $R_2$ | $R_3$ |
|---|---|---|---|---|
| Sarcodictyin A | ($A_1$) | Me | H | (E)u |
| Sarcodictyin B | ($A_1$) | Et | H | (E)u |
| Sarcodictyin C | ($A_1$) | Me | OH | (E)u |
| Sarcodictyin D | ($A_1$) | Me | OAC | (E)u |
| Sarcodictyin E | ($A_1$) | Me | OH | (Z)u |
| Sarcodictyin F | ($A_2$) | Me | OH | (E)u |

In the above Table 1:
the symbol Me means methyl;
the symbol Et means ethyl;
the symbol OAc means $OCOCH_3$.

the symbols (E)u and (Z)u represent, respectively, the (E) and (Z) urocanoyl moiety of formula

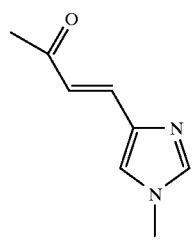

(E) urocanoyl

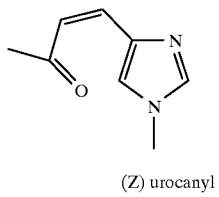

(Z) urocanyl

In particular, the above reported Sarcodictyins A to F may be useful as therapeutic agents in the treatment of cancers in human or animal beings, by virtue of their cytotoxic, antitumor activity. The cancer may be selected from sarcomas, carcinomas, lymphomas, neuroblastomas, melanomas, myelomas, Wilms tumor, leukemias and adenocarcinomas.

The Sarcodictyins of the invention may be obtained by isolation from the Mediterranean Stoloniferan Coral "Sarcodictyon Roseum" (Rolandia rosea) (Forbes 1847) according to the method reported in Helvetica Chimica Acta Vol. 70, 1987, page 2025.

The biological activity of the Sarcodictyins of the invention was demonstrated by (a) "in vitro" test to evaluate their activity in promoting the tubulin assembly and (b) "in vitro" test to evaluate their cytotoxic activity both on L 1210 cells and L 1210 cells resistant to Doxorubicin (L 1210/Dx).

As an example, the activity of Sarcodictyin A (internal code FCE 29123) and Sarcodictyin C (internal code FCE 29119) was evaluated according to the methods described in tests (a) and (b).

(a) Tubulin assembly test

Calf brain tubulin was prepared by two cycles of assembly-disassembly (Shelanski M. L., Gaskin F. and Cantor C. R., Proc. Natl.Acad.Sci. U.S.A. 70, 765–768, 1973) and stored in liquid nitrogen in MAB (0.1 M MES, 2.5 mM EGTA, 0.5 mM $MgSO_4$, 0.1 mM EDTA, 0.1 mM DTT, pH 6.4).

All the experiments were carried out on protein stored for less than 4 weeks.

Before each experiment, tubulin was kept 30 min at 4° C. Assembly was monitored by the method of Gaskin et al. (Gaskin F., Cantor C. R. and Shelanski M. L., J.Molec.Biol. 89, 737–758, 1974).

The cuvette (1 cm path) containing tubulin (1 mg/ml) and 1 mM GTP was shifted to 37° C. and continuous turbidity measurements were made at 340 nm on a Perkin-Elmer 557 double wavelength, double beam spectrophotometer equipped with an automatic recorder and a thermostatically regulated sample chamber.

After 30 minutes, 4 mM $CaCl_2$ was added and depolymerisation was measured for 10 minutes as decreased turbidity.

At regular intervals of 15 minutes scaled doses of the tested compounds were added and variations in the turbidity were monitored.

Data are expressed as percentage of repolymerization induced by the tested compounds.

The obtained results are reported in Table 2

TABLE 2

| COMPOUND | dosage ($\mu M$) | tubulin assembly (%) |
|---|---|---|
| Sarcodictyin A | 4 | 70 |
| (FCE 29123) | 40 | 162 |
| Sarcodictyin C | 3.9 | 112 |
| (FCE 29119) | 39 | 173 |

The above tabulated data clearly demonstrate that the tested Sarcodictyins are able to promote tubulin repolymerization even in the presence of $CaCl_2$ which usually inhibits tubulin assembly.

As it is well known in the art, microtubules are among the most strategic subcellular targets of anticancer chemotherapeutics (Rowinsky et al., Review, Vol. 82, No. 15, Aug. 1, 1990).

Unlike classical antimicrotubule agents like colchicine and the vinca alkaloids which induce depolymerization of microtubules, Sarcodictyns seem to posses a mechanism of action similar to that of Taxol, one of the most interesting anticancer agents emerged from the screening of natural products, by inducing tubulin polymerization and forming extremely stable and nonfunctional microtubules.

Sarcodictyins can therefore be useful as therapeutic antineoplastic agents in the treatment of cancers in human or animal beings, in view of their ability to catalize rapid microtubule formation and stabilization which cause suspension of cellular division in the tumor cells.

(b) Cell cultures and drug sensitivity assay

L1210 and L1210/DX (Doxorubicin resistant) murine leukemia cell lines were grown in vitro as a stationary suspension culture in RPMI 1640 medium (GIBCO, Grand island, N.Y.) supplemented with 10% fetal calf serum (Flow, Irwine, UK), 2 mM L-glutamine (Gibco Europe, Glasgow, UK), 10 $\mu M$ β-mercaptoethanol, 100 Units/ml penicillin and 100 $\mu g$/ml streptomycin.

Exponentially growing cells were seeded ($1 \times 10^5$ cell/ml) in 12-well/plates (Costar, Cambridge, Mass.) and various concentrations of tested compounds were added immediately after seeding.

The plates were incubated at 37° C. in a humidified, 5% $CO_2$ atmosphere for 48 hr.

Inhibition of cell growth was evaluated by counting surviving cells in a ZBI Coulter Counter (Hialeah, Fla.). The 50% inhibitory concentration ($IC_{50}$) was calculated on the derived concentration-response curve. For each tested compound concentration, duplicate cultures were used.

The obtained results are reported on Table 3

TABLE 3

| | $ID_{50}$ (nM)* | | |
|---|---|---|---|
| Compound | L1210 | L1210/DX | R.I. |
| Sarcodictyin A (FCE 29123) | 539.2 ± 97.7 | 754.5 ± 80.3 | 1.4 |
| Sarcodictyin C (FCE 29119) | 408.5 ± 21.3 | 5787.0 ± 182.6 | 14.2 |

*48 h treatment $$R.I. = Resistance\,index = \frac{ID_{50}\,L1210/DX}{ID_{50}\,L1210}$$

As evident from the above tabulated data, Sarcodictyins exhibit a good "in vitro" cytotoxic activity both on L1210 and L1210 cells resistant to Doxorubicin (L1210/Dx).

In view of their effectiveness on L 1210/DX cells, the Sarcodictyins can be useful in the treatment of a tumor resistant to a chemotherapeutic agent, such as, e.g., an anthracycline glycoside, in particular Doxorubicin.

A human or animal being can be treated by a method which comprises the administration thereto of a pharmaceutically effective amount of a compound selected from Sarcodictyin A, Sarcodictyin B, Sarcodictyin C, Sarcodictyin D, Sarcodictyin E and Sarcodictyin F.

The condition of the human or animal being can thereby be improved.

The Sarcodictyins of the invention can be administered in a variety of dosage forms, e.g. orally, in the form of tables, capsules, sugar or film coated tablets, liquid solutions or suspensions; rectally in the form of suppositories; parenterally, e.g. intramuscularly, or by intravenous injection or infusion.

The dosage depends on the age, weight, conditions of the patient and on the administration route; for example, the dosage adopted for oral administration to adult humans, e.g., for the representative compound of the invention FCE 29213 (Sarcodictyin A) may range from about 0.01 g to about 1 g per day.

The invention includes also pharmaceutical compositions comprising a Sarcodictyin of the invention as an active principle in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, destrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethycellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations.

Said pharmaceutical preparations may be manufactured in known manner, for example by means of mixing, granulatilng, tabletting, sugar-coating, or film-coating processes.

The liquid dispersions for oral administration may be, e.g., syrups, emulsions and suspensions.

The syrups may contain as carrier, for example, saccharose or saccharose with glycerine and/or mannitorl and/or sorbitol.

The suspensions and the emulsions may contain as carrier, for example, a natural gum, agar, sodium alginate, pectin, methylcellulose, carboxymethyl-cellulose, or polyvinyl alcohol.

The suspension or solution for intramuscular injections may contain, e.g., together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or preferably they may be in the form of sterile, acqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

We claim:

1. A pharmaceutical composition suitable for administration to a human or mammal comprising as an active ingredient a pharmaceutically effective amount of a chemical compound selected from the group consisting of Sarcodictyin A, Sarcodictyin B, Sarcodictyin C, Sarcodictyin D, Sarcodictyin E, and Sarcodictyin F, said composition containing in addition to said active ingredient a non-toxic, pharmaceutically acceptable, inactive substance selected from diluents, lubricants, binding agents, effervescing mixtures, dyestuffs, sweeteners, wetting agents, carriers or thickening agents.

2. A pharmaceutical composition suitable for administration to a human or mammal as set forth in claim 1, wherein said composition is in solid oral form and contains a diluent selected from the group consisting of lactose, dextrose, saccharose, cellulose, corn starch and potato starch.

3. A pharmaceutical composition as set forth in claim 1, wherein said composition is a liquid suitable for oral administration and is in the form of a syrup, emulsion or suspension.

4. The composition of claim 1, wherein said pharmaceutical composition is in the form of a suspension or solution suitable for injection and contains a pharmaceutically acceptable liquid carrier selected from the group consisting of sterile water, olive oil, ethyl oleate and glycols.

5. The pharmaceutical composition as set forth in claim 1, wherein said composition is in the form of a suppository and contains a carrier selected from the group consisting of cocoa butter, polyethylene glycol, polyoxyethylene sorbitan fatty acid ester surfactant and lecithin.

6. A pharmaceutical composition suitable for administration to a human or mammal comprising as an active ingredient a pharmaceutically effective amount of a chemical compound selected from the group consisting of Sarcodictyin A, Sarcodictyin B, Sarcodictyin C, Sarcodictyin D, Sarcodictyin E, and Sarcodictyin F, and a pharmaceutically acceptable carrier and/or diluent.

7. A pharmaceutical composition as claimed in claim 1, wherein the pharmaceutically effective amount ranges from about 0.01 g to about 1 g per day.

* * * * *